United States Patent
Clarke et al.

(10) Patent No.: US 8,515,135 B2
(45) Date of Patent: Aug. 20, 2013

(54) PLL ADJUSTMENT TO FIND AND MAINTAIN RESONANT FREQUENCY OF PIEZO ELECTRIC FINGER PRINT SENSOR

(75) Inventors: David Brian Clarke, Melbourne, FL (US); Christian Liautaud, Boca Raton, FL (US)

(73) Assignee: Sonavation, Inc., Palm Beach Gardens, FL (US)

( * ) Notice: Subject to any disclaimer, the term of this patent is extended or adjusted under 35 U.S.C. 154(b) by 1073 days.

(21) Appl. No.: 12/149,664

(22) Filed: May 6, 2008

(65) Prior Publication Data

US 2009/0279746 A1 Nov. 12, 2009

(51) Int. Cl.
*G06K 9/00* (2006.01)
*H01L 41/00* (2006.01)
*H02N 2/00* (2006.01)

(52) U.S. Cl.
USPC .................. 382/115; 310/318; 310/323.21

(58) Field of Classification Search
USPC .................. 382/115; 310/318, 323.21
See application file for complete search history.

(56) References Cited

U.S. PATENT DOCUMENTS

| | | | |
|---|---|---|---|
| 6,094,499 A * | 7/2000 | Nakajima et al. | 382/124 |
| 6,241,288 B1 * | 6/2001 | Bergenek et al. | 283/67 |
| 6,405,135 B1 * | 6/2002 | Adriany et al. | 702/5 |
| 6,898,299 B1 * | 5/2005 | Brooks | 382/115 |
| 7,110,579 B2 * | 9/2006 | Hashimoto | 382/124 |
| 7,226,164 B2 * | 6/2007 | Abourizk et al. | 351/206 |
| 7,646,893 B2 * | 1/2010 | Yamada et al. | 382/115 |
| 2002/0082830 A1 * | 6/2002 | Eide | 704/231 |
| 2004/0052406 A1 * | 3/2004 | Brooks | 382/115 |
| 2005/0223236 A1 * | 10/2005 | Yamada et al. | 713/186 |
| 2006/0034493 A1 * | 2/2006 | Shimamura et al. | 382/115 |
| 2006/0072843 A1 * | 4/2006 | Johnston | 382/254 |

* cited by examiner

*Primary Examiner* — John Strege
(74) *Attorney, Agent, or Firm* — Kenneth J. Lukacher Law Group

(57) ABSTRACT

Provided is a method for determining a resonant frequency of a biometric sensor. The method includes obtaining first pixel data from a first scan by scanning the biometric sensor with a first frequency. Second pixel data is obtained from a second scan by scanning the biometric sensor with a second frequency that is different from the first frequency. A respective first and second reference value is calculated from the first and the second pixel data. A highest reference value is determined from the first and the second reference values. The first or the second frequency is selected as the resonant frequency based on the highest reference value.

27 Claims, 13 Drawing Sheets

PLL ADJUSTMENT TO FIND AND MAINTAIN RESONANT FREQUENCY OF PIEZO ELECTRIC FINGER PRINT SENSOR

BACKGROUND OF THE INVENTION

1. Field of the Invention

The present invention relates to biometric sensor optimization. More particularly, the present invention relates to optimizing performance of a biometric sensor.

2. Related Art

In the field of biometric image analysis, traditional techniques sample an image, such as a fingerprint, as the image is sensed by a sensing mechanism. This sensing mechanism, such as a pressure and/or acoustic impedance-sensitive piezoelectric fingerprint sensor, captures images of the fingerprint. Ridges and valleys of the fingerprint vary pressure and/or acoustic impedance on different parts of the piezoelectric sensor to form light and dark portions of the captured image.

The sensing ability of conventional biometric sensors, and their processing circuits, suffers from many shortcomings due to effects of changing environmental conditions, sensor manufacturing variations, and conditions of the fingers themselves. These conventional biometric sensors are also susceptible to temperature variations, air pressure, and humidity. These changes lead to problems like variations in the sensor's resonant frequency and sensor accuracy, thus degrading sensor performance and resulting in a loss of information.

Conventional biometric sensors also suffer from manufacturing variations. Manufacture of piezoelectric sensors requires creating an array of piezoelectric sensing elements. The manufacturing process varies thickness from sensor to sensor, affecting response of the sensing elements to finger pressure and/or acoustic impedance and thus sensor performance. These variations in resonant frequency degrade sensor performance and lead to changes in signal level and bias of the sensor's output that are unmitigated by conventional processing circuits.

What is needed, therefore, is a biometric sensor optimization technique that reduces the effects of the environment, manufacturing variations, and finger conditions as noted above in conventional approaches.

SUMMARY OF THE INVENTION

The present invention is directed to a method for determining a resonant frequency of a biometric sensor. The method includes obtaining first pixel data from a first scan by scanning the biometric sensor with a first frequency. Second pixel data is obtained from a second scan by scanning the biometric sensor with a second frequency that is different from the first frequency. A respective first and second reference value is calculated from the first and the second pixel data. A highest reference value is determined from the first and the second reference values. The first or the second frequency is selected as the resonant frequency based on the highest reference value.

Further embodiments, features, and advantages of the present invention, as well as the structure and operation of the various embodiments of the present invention are described in detail below with reference to accompanying drawings.

BRIEF DESCRIPTION OF THE DRAWINGS/FIGURES

The accompanying drawings illustrate the present invention and, together with the description, further serve to explain the principles of the invention and to enable one skilled in the pertinent art to make and use the invention.

In the drawings, like reference numbers generally indicate identical, functionally similar, and/or structurally similar elements. The drawing in which an element first appears is usually indicated by the leftmost digit(s) in the reference number.

DETAILED DESCRIPTION OF THE INVENTION

This specification discloses one or more embodiments that incorporate the features of this invention. The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Furthermore, when a particular feature, structure, or characteristic is described in connection with an embodiment, it is submitted that it is within the knowledge of one skilled in the art to effect such feature, structure, or characteristic in connection with other embodiments whether or not explicitly described.

Overview

Embodiments provide methods, apparatus, and computer program products for determining a resonant frequency of a biometric sensor and using this information to improve image quality. Once determined, the sensor's resonant frequency is maintained by adjusting a phase-locked loop (PLL) to the sensor's resonant frequency or an offset of the sensor's resonant frequency. Determining and maintaining image acquisition based on the sensor's resonant frequency mitigates effects of environmental conditions and manufacturing variations.

The sensor's resonant frequency is detected by applying a different frequency to the sensor for each scan while scanning an image, such as a fingerprint, with the sensor. Image data from the scans is processed to determine which applied frequency returns an image providing a high pixel value, relative to pixel values returned at other applied frequencies or vice versa. To decrease processing time, a coarse scan followed by a fine scan can be applied to the sensor.

Exemplary Apparatus

Figure 1:
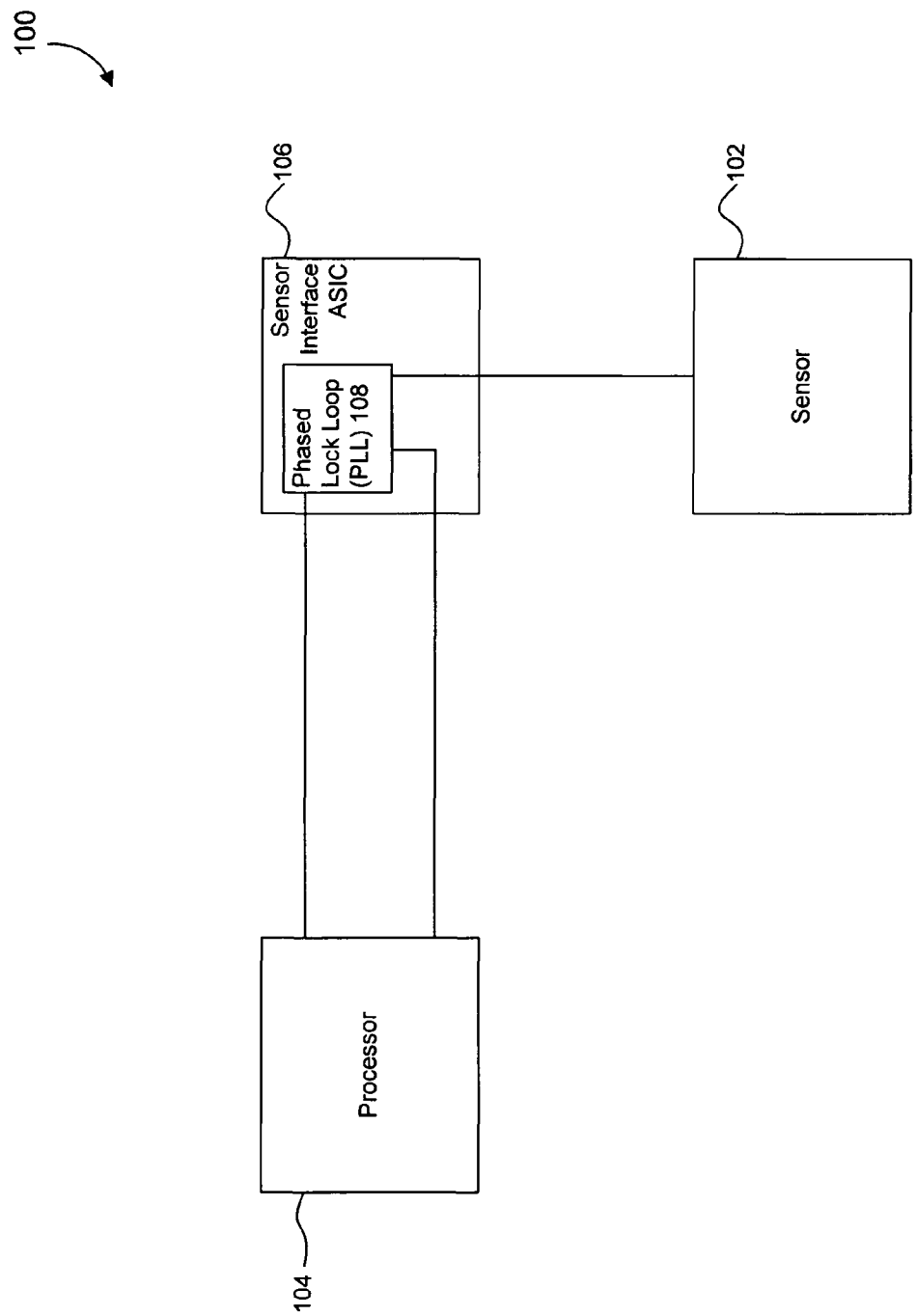
FIG. 1 is an illustration of a biometric sensing device.

FIG. 1 is an illustration of an exemplary biometric sensing device 100. In FIG. 1, the biometric sensing device 100 includes a sensor 102 for obtaining biometric data (e.g. fingerprint data). The sensor 102 can be, for example, an acoustic (non-optical) impediography-type device or a piezoelectric device. The sensor 102, however, is not limited to these types of sensors. Other types of sensors can be used in the biometric sensing device 100. The sensor 102 captures at least a partial image of a sampled biometric feature, such as a fingerprint. A processor 104 controls the sensor 102 and processes image data provided by the sensor 102 via a sensor interface application specific integrated circuit (ASIC) 106. Further, the processor 104 executes a method as described herein. The processor 104 receives image data, also known as pixel data, produced by the sensor 102 and provides frequency adjustment commands to vary a frequency of a PLL 108. The sensor interface 106 and the PLL 108 can be part of the processor 104. Thus, the sensor 102 can be coupled directly to the processor 104. At least a part of the apparatus described herein can be deposited on a substrate.

Figure 2:
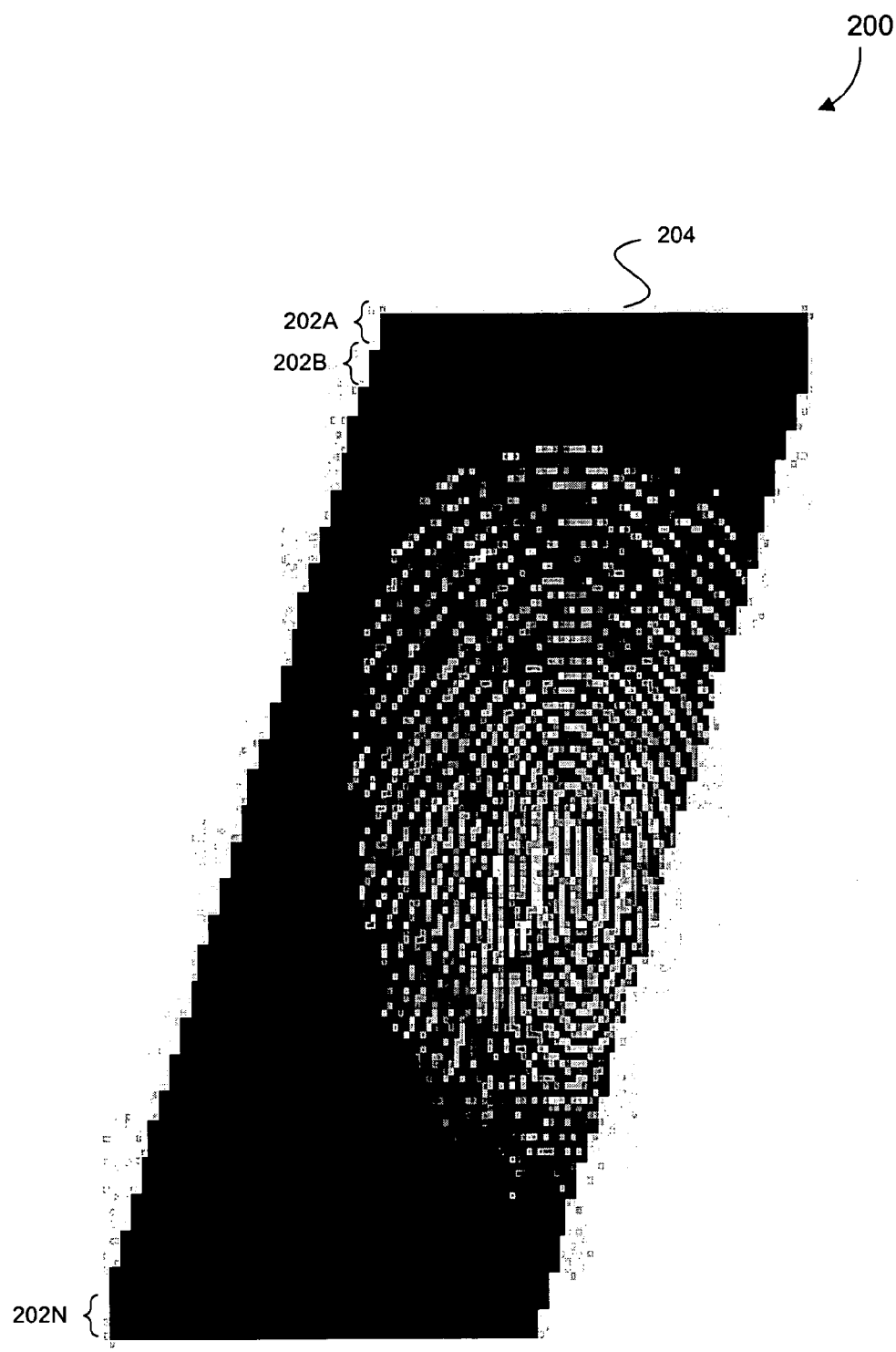
FIG. 2 is an illustration of image data produced by a swipe-style piezoelectric fingerprint sensor.

FIG. 2 is an illustration of exemplary image data 200 produced when the sensor 102 is a swipe-style piezoelectric sensor. When sampling a feature, the sensor 102 of FIG. 1 can generate an exemplary series of partial images 202A, B, ..., N. The sensor 102 performs a scan to produce each of the partial images 202A, B, ..., N. As used herein, the term "scan" is used interchangeably with the term "slice." As used herein, each scan can also be referred to as a slice. Each of the partial images 202A, B, ..., N contains a plurality of pixels. Each pixel has a pixel value 204.

Determining a Sensor's Resonant Frequency

Figure 3:
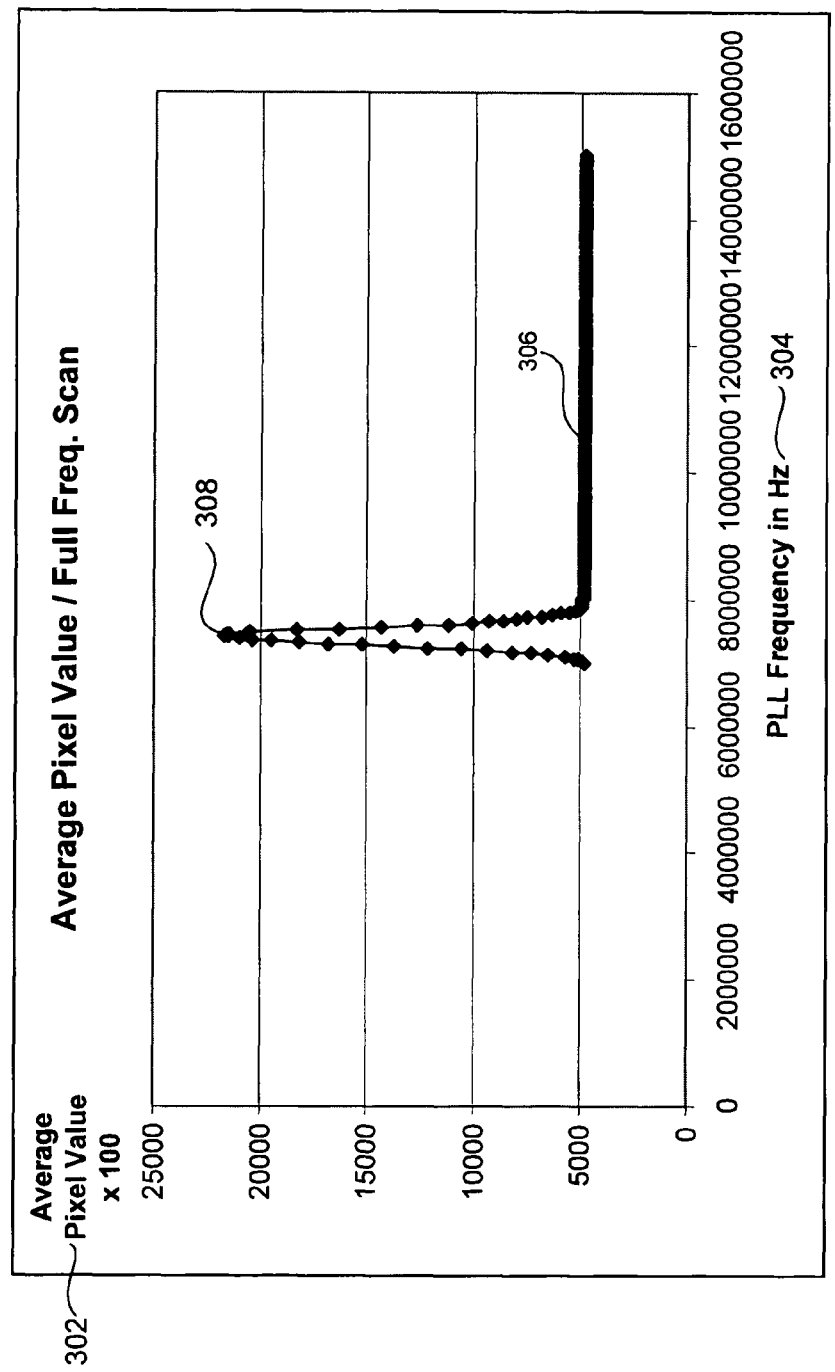
FIG. 3 is a graphical illustration of image data produced by an exemplary full-frequency scan.

FIGS. 3 through 7 shows an method to determine a sensor's resonant frequency such as a typical resonant frequency that can be in a range from 7-15 MHz. The resonant frequency of the sensor 102 is determined by applying a range of frequencies to the sensor 102. Simultaneously, scans are performed by the sensor 102 at these different frequencies to produce respective image data. The image data for each scan has an average pixel value that is frequency-dependent. Thus, when the sensor 102 scans at different frequencies, the average pixel value changes. In an example, spacing between frequencies during scanning can be less than 100 kHz. An example of applying a range of frequencies to the sensor 102 while scanning an image is shown in FIG. 3.

FIG. 3 is a graphical illustration of an exemplary full-frequency scan 300 of applied frequencies 304 ranging from 7-15 MHz that is used to determine the average pixel value 302. The resonant frequency illustrated in FIG. 3 is 7.45 MHz. The processor 104 processes image data 306 from the scan 300 to determine which applied frequency 304 returns image data 306 providing a highest pixel value 308, relative to pixel values returned at the other applied frequencies 304. To identify the highest pixel value 308, the pixel data from each scan 300 can be added, or a mean computed, to determine a result for each scan 300 so that pixel data from each scan 300 can be compared.

For example, an average pixel value 302 for each scan 300 that is a part of a plurality of scans can be determined. The average pixel value 302 for each scan 300 is then compared to average pixel values from other scans to determine which applied frequency 304 returns the highest average pixel value 308. In a further example, a sensor 102 using 8-bit pixels results in a mean pixel value 304 between zero and 255, with zero representing a "black" pixel and 255 representing a "white" pixel. Thus, at the resonant frequency, the sensor 102 returns the whitest image. The frequency of the PLL 108 can then be set to approximately equal the resonant frequency as determined by the scan 300. Alternatively, the PLL 108 can be adjusted to approximately a harmonic or approximately a sub-harmonic of the resonant frequency as determined by the scan 300.

Coarse and Fine Frequency Scans

Figure 4:
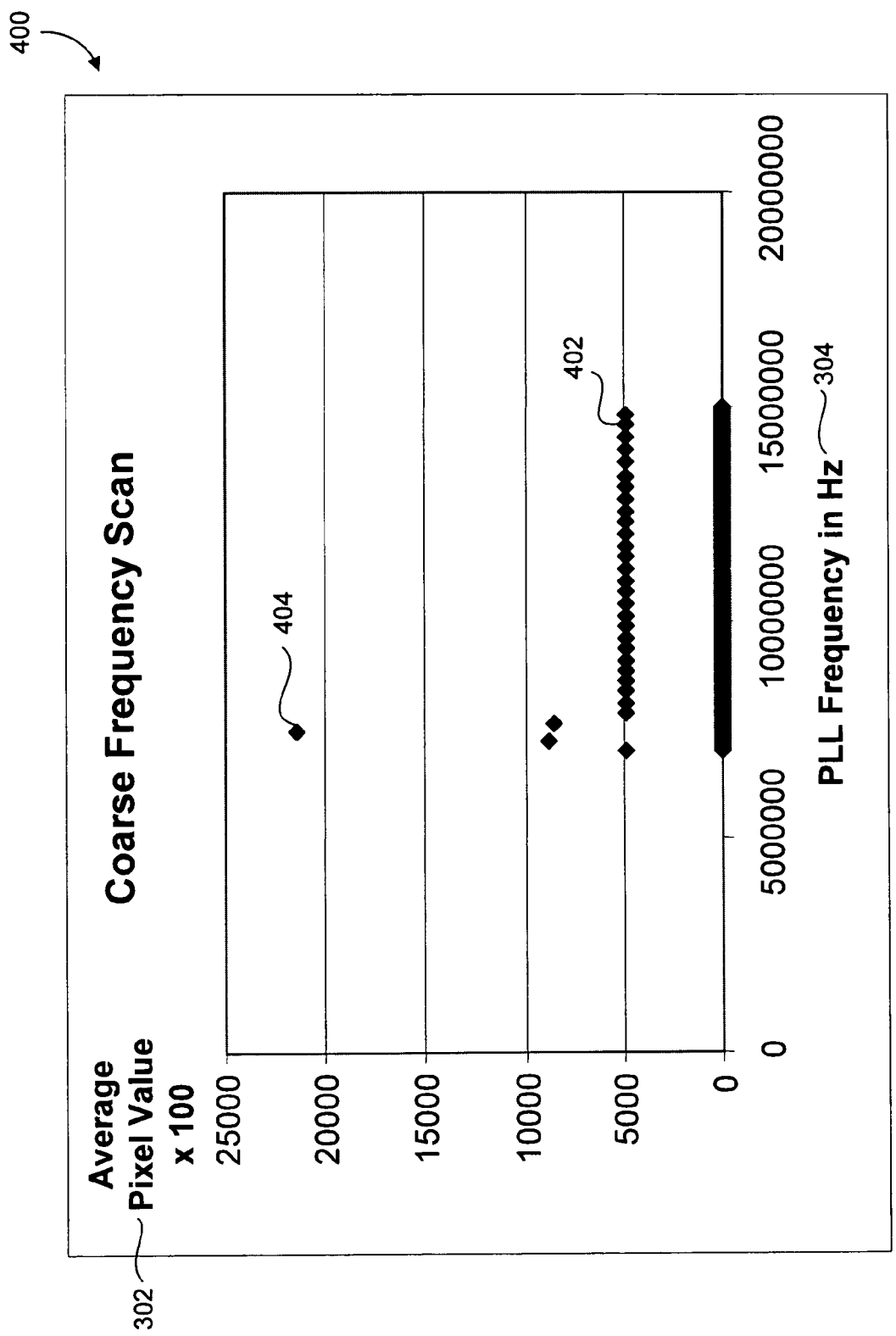
FIG. 4 is a graphical illustration of image data produced by an exemplary coarse frequency scan.
Figure 5:
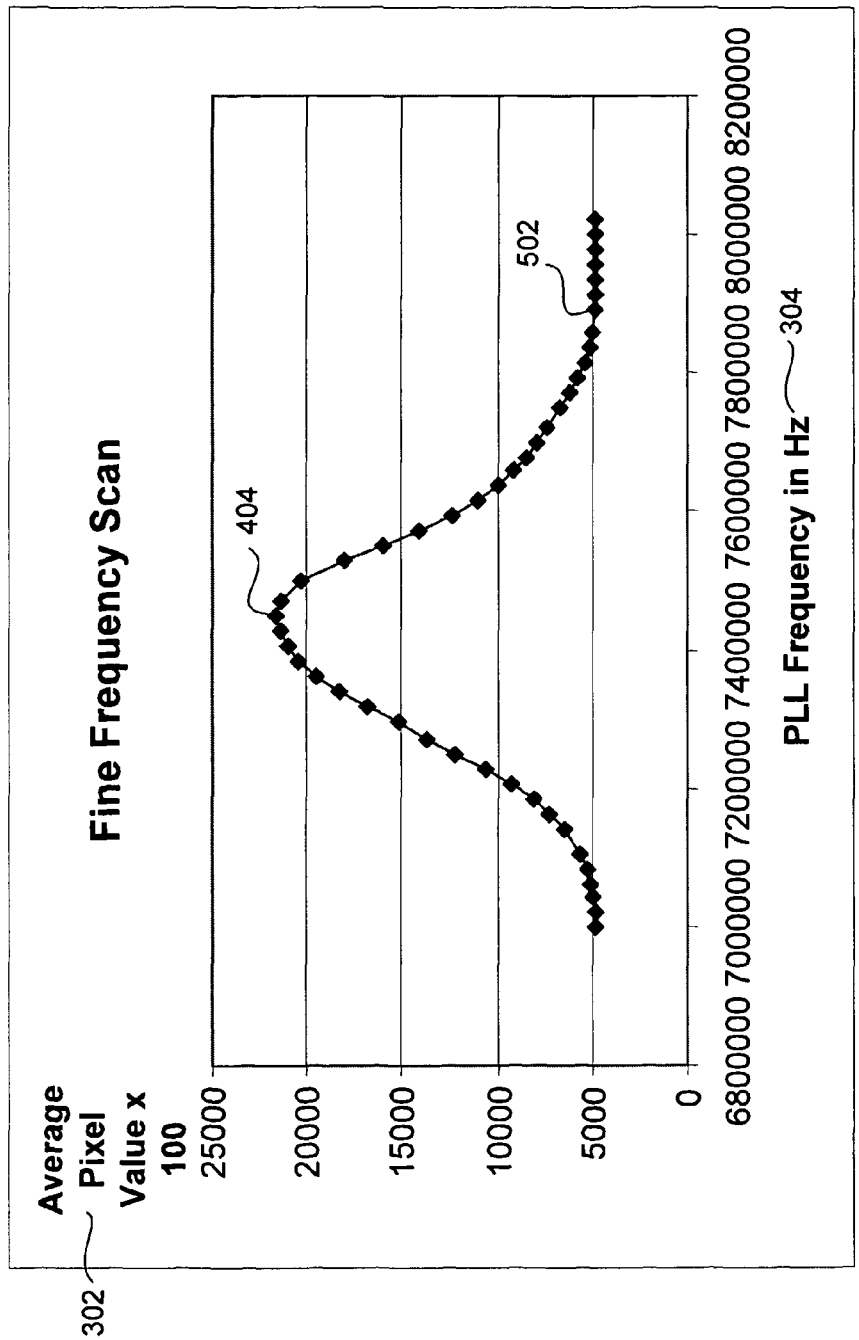
FIG. 5 is a graphical illustration of image data produced by an exemplary fine frequency scan.

A time required to determine the sensor's resonant frequency can be reduced by dividing a scan into a combination of a coarse frequency scan 400 that is followed by an optional fine frequency scan 500. FIG. 4 is a graphical illustration of image data 402 produced by an exemplary coarse frequency scan 400. FIG. 5 is a graphical illustration of image data 502 produced by an exemplary fine frequency scan 500. The coarse frequency scan 400 approximately determines the resonant frequency 404 by scanning with a frequency spacing that is higher than that of the fine frequency scan 500. The coarse frequency scan 400 can also scan a bandwidth of frequencies that is greater than a bandwidth of the fine frequency scan 500. As can be seen in FIG. 4, when the applied scan frequency 304 approximately equals the sensor's resonant frequency, the average pixel value 302 peaks. The frequencies illustrated in FIG. 4 as having the average pixel value 302 of zero represent frequencies that are not scanned during the coarse frequency scan 400.

Following the coarse frequency scan 400, the fine frequency scan 500 further determines the resonant frequency 404 with an accuracy greater than that of the coarse frequency scan 400. The fine frequency scan 500 scans frequencies within a frequency difference from the peak determined by the coarse frequency scan 400. As an example, the frequency difference from the peak can be substantially 250 KHz. The fine frequency scan 500 scans with a narrower frequency spacing between scan frequencies than the coarse frequency scan 400. Also, the fine frequency scan 500 can scan a bandwidth of applied frequencies 304 that is narrower than that of the coarse frequency scan 400. After the coarse frequency scan 400 or the fine frequency scan 500, the frequency of the PLL 108 can be set to approximately equal the resonant frequency as determined by the scans. Alternatively, the PLL 108 can be adjusted to a harmonic or a sub-harmonic of the resonant frequency as determined by the fine frequency scan 500.

Figure 13:
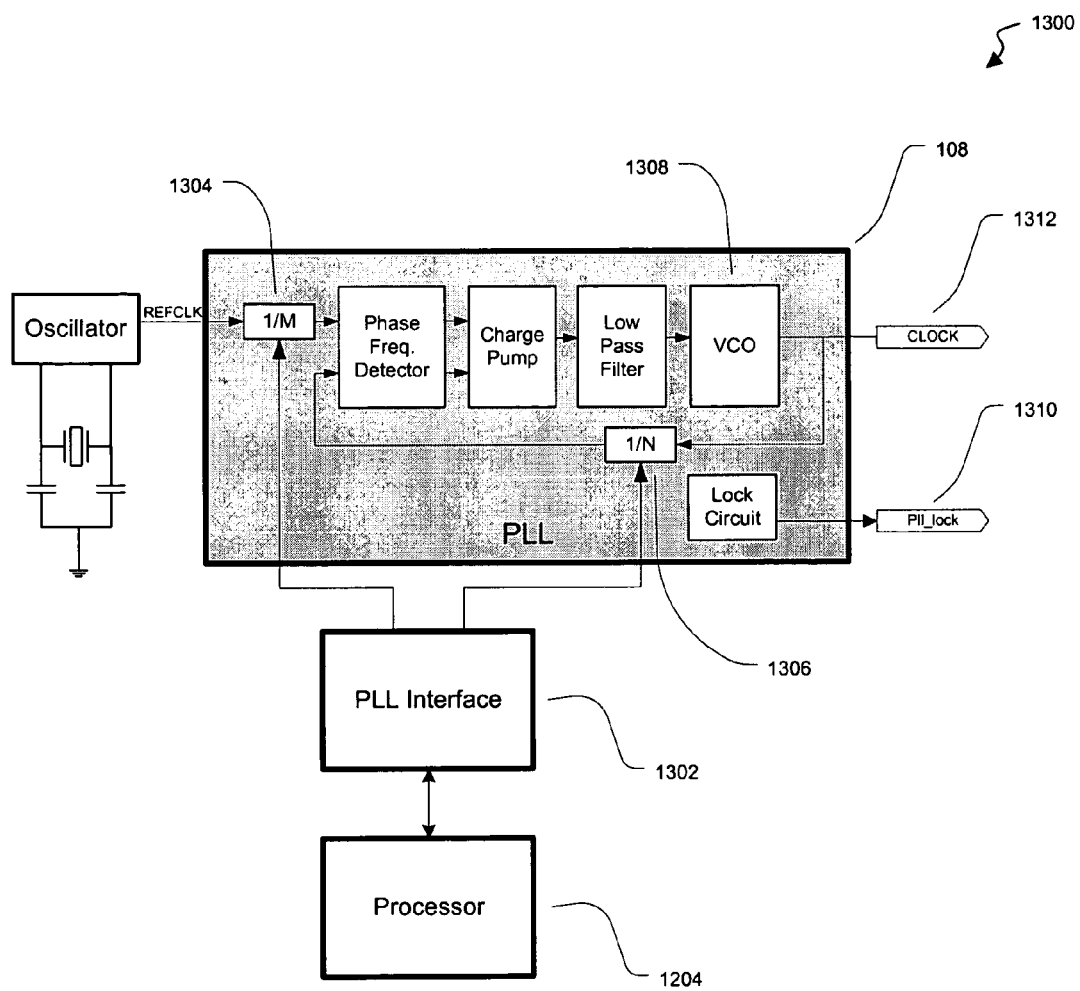
FIG. 13 is a block diagram illustration of an exemplary system to maintain PLL lock.

FIG. 13 is a block diagram illustration of an exemplary system 1300 to maintain PLL lock. During the fine frequency scan 500, the frequency of the PLL 108 can be adjusted such that the PLL 108 stays in lock. This further decreases a time to perform the fine frequency scan 500. Adjustment of the frequency of the PLL 108 is done by using a PLL interface 1302 that presents M and N dividers 1304, 1306 of the PLL 108 at the same time. Traditional PLL systems present the M and N dividers at different times. This causes a frequency of a VCO 1308 inside the PLL 108 to go outside an intended frequency and/or operating constraint to maintain a PLL lock 1310. When the M and N dividers 1304, 1306 are presented values at the same time and the resulting frequency change is small, the PLL lock 1310 is maintained and the VCO 1308 and resulting frequency of a PLL output clock 1312 stay within operating constraints. A processor, such as processor 1204, is coupled to the PLL interface 1302.

Limiting a Coarse Frequency Scan

Figure 6:
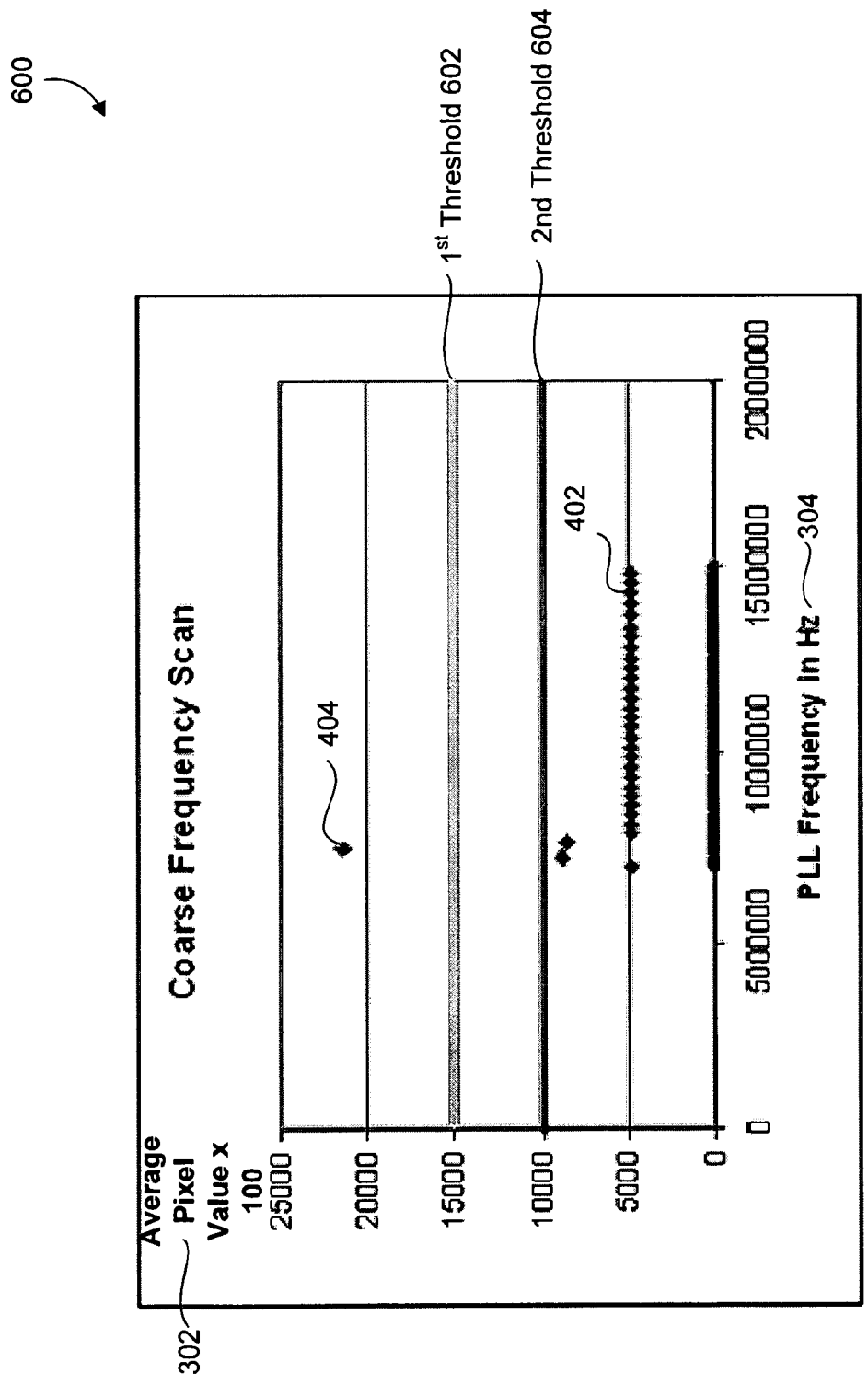
FIG. 6 is a graphical illustration of image data produced by a coarse frequency scan, a first threshold, and a second threshold.

The time required to perform a scan of the sensor 102 can be reduced by limiting a bandwidth of the coarse frequency scan 400, once it is probable that the average pixel value 302 peak has been found. FIG. 6 is a graphical illustration of a graph 600 of the coarse frequency scan 400 with the addition of a first threshold 602 and a second threshold 604 that assist in assessing the probability that the average pixel value 302 peak has been found. As shown in FIG. 6, when scanning from a low applied frequency 304 to a high applied frequency 304, the resonant frequency can be identified early in the coarse frequency scan 400 by identifying a first applied frequency at which the average pixel value 302 exceeds the first threshold 602 as well as a second applied frequency at which the average pixel value subsequently falls below the second threshold 604. Time spent scanning the applied frequencies 304 that are higher than the second applied frequency is wasted. As is shown in FIG. 7 and described below, when the second threshold 604 is passed, the coarse frequency scan 400 can stop.

Figure 7:
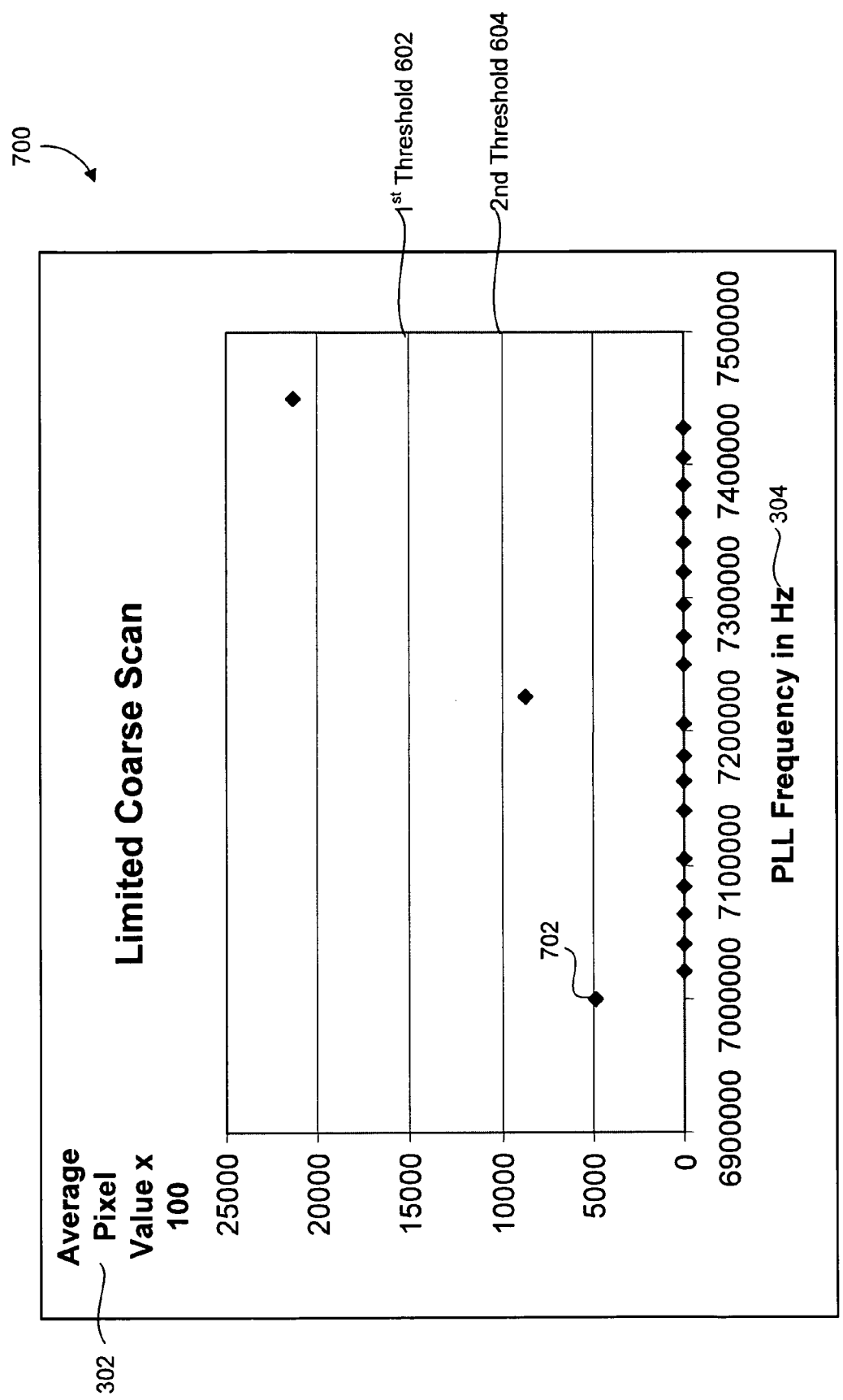
FIG. 7 is a graphical illustration of image data produced by a limited coarse frequency scan.

FIG. 7 is a graphical illustration of image data 702 produced by an exemplary limited coarse frequency scan 700. The limited coarse frequency scan 700 reduces time required to scan the sensor 102 by eliminating a need to scan additional applied frequencies 304 after identification of the average pixel value 302 peak. During the limited coarse frequency scan 700, the average pixel value 302 is compared to the first threshold 602 and the second threshold 604. If the average pixel value 302 is greater than the first threshold 602 and subsequently less than the second threshold 604, then the limited coarse frequency scan 700 ceases. This results in an abbreviated scan when the sensor 102 has a resonant frequency that is in a lower-frequency part of the applied frequencies 304 of the coarse frequency scan 400. The fine frequency scan 500 as described above can then follow the limited coarse frequency scan 700.

Following determination of the sensor's resonant frequency as determined by the limited coarse frequency scan 700, the PLL 108 can be set to approximately the determined resonant frequency. Alternatively, the PLL 108 can be adjusted to approximately a harmonic or approximately a sub-harmonic of the resonant frequency as determined by the limited coarse frequency scan 700. The frequencies illustrated in FIG. 7 as having the average pixel value 302 of zero represent frequencies that are not scanned.

In an example, where the range of pixel values 302 from the image data is from zero to 255, the first threshold 602 can equal a pixel value 302 of one-hundred and fifty. The second threshold 604 can equal a pixel value 302 of one-hundred. These threshold values are exemplary. In the alternative, the first threshold 602 and the second threshold 604 can equal other pixel values 302, so long as the first threshold 602 has a pixel value 302 greater than that of the second threshold 604.

Maintaining the Sensor's Resonant Frequency

Figure 8:
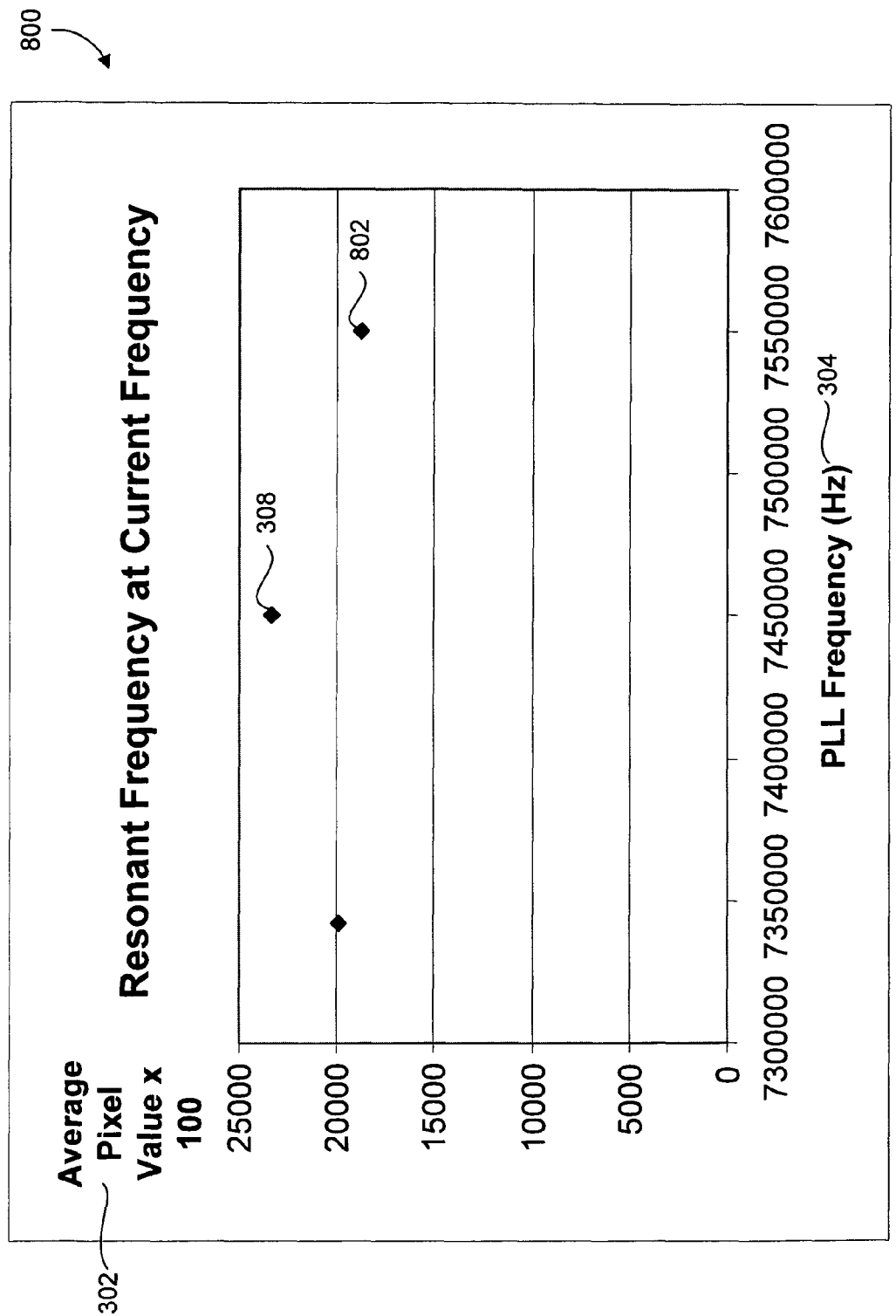
FIG. 8 is a graphical illustration of image data produced when a current scan frequency returns the highest pixel value.
Figure 9:
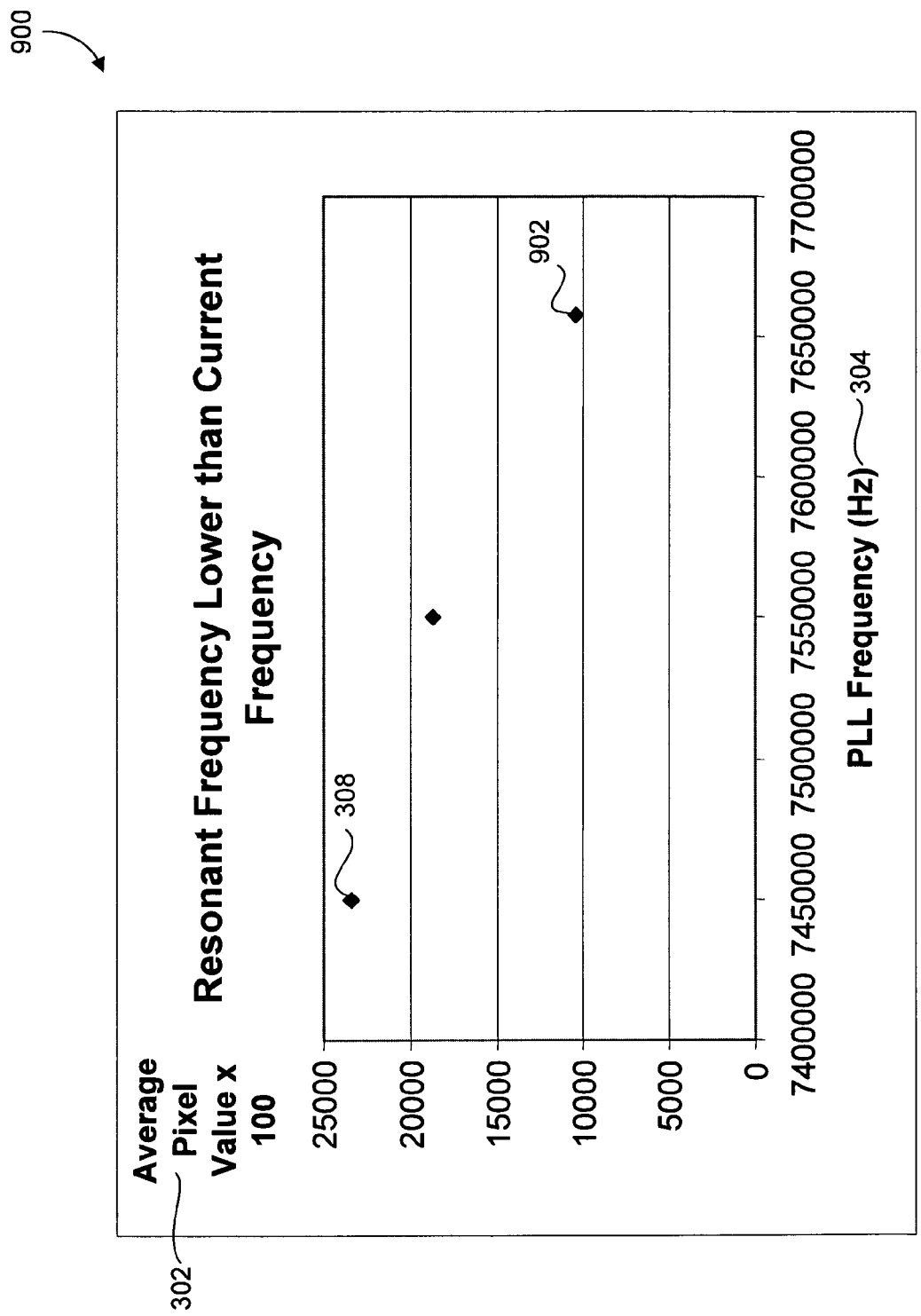
FIG. 9 is a graphical illustration of image data produced when a lower scan frequency returns the highest pixel value.
Figure 10:
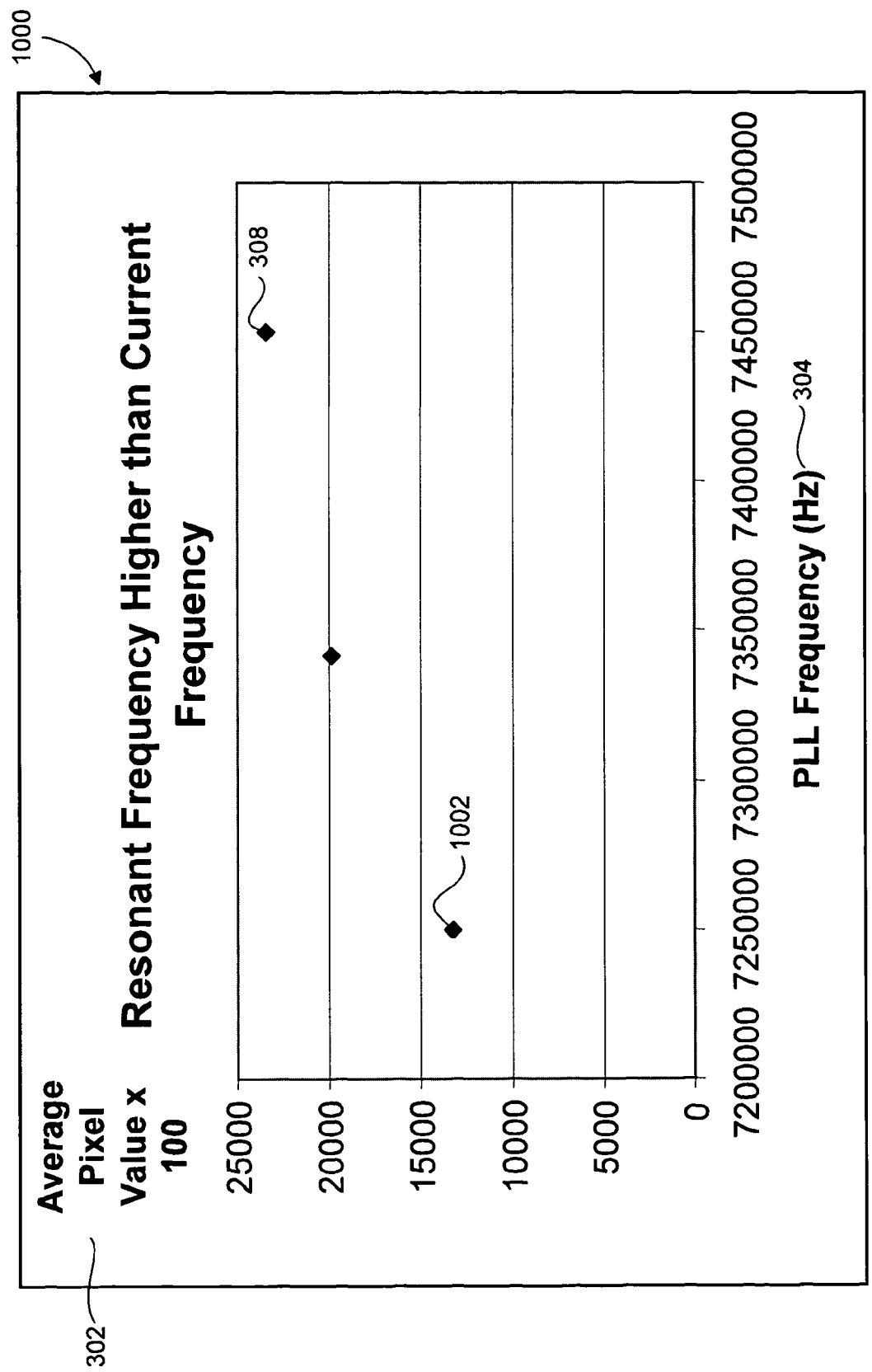
FIG. 10 is a graphical illustration of image data produced when a higher scan frequency returns the highest pixel value.

The resonant frequency of the sensor 102 can change due to effects of temperature change, such as that occurring when a finger is placed on the sensor 102. FIGS. 8 through 10 illustrate how the changes in the resonant frequency of the sensor 102 are determined following an initial determination of the resonant frequency. The overall process to maintain the sensor's resonant frequency has two interrelated processes, the first is a detection process and the second is a compensation process. Detection and compensation of changes in the sensor's resonant frequency can occur periodically or dynamically.

During the detection process, changes in the resonant frequency are detected by scanning the sensor 102 with at least three frequencies. The first frequency scan is at a current frequency (i.e. a previously-determined resonant frequency), the second scan is at a frequency lower than the current frequency, and the third scan is at a frequency higher than the current frequency. These scans return image data from which an average pixel value 302 is determined. The highest pixel value from the three scans indicates either a change or no change in the resonant frequency. If the lower frequency scan results in the highest pixel value 302, a lower frequency is needed for resonance. If the higher frequency scan results in the highest pixel value 302, a higher frequency is needed for resonance. If the current frequency scan results in the highest pixel value 302, no change is needed. The PLL 108 frequency can be adjusted accordingly in a direction based on the determined change during the compensation process.

The PLL 108 need not be adjusted to exactly equal the lower frequency or the higher frequency. During the compensation process, the PLL 108 frequency can be adjusted by an amount other than the frequency difference between the current frequency and either the lower frequency or the higher frequency. Since the changes in the resonant frequency tend to be minor, a relatively large difference between the current frequency and either the lower frequency or the higher frequency can be used to detect the change in resonant frequency, followed by a relatively smaller adjustment to the PLL 108 frequency. The detection and compensation process can then repeat and the PLL 108 frequency adjusted incrementally. The compensation process ceases when no further adjustment to PLL 108 frequency is indicated as required by the detection process. The detection process then continues to detect further changes in the resonant frequency of the sensor 102.

FIG. 8 is a graphical illustration of an exemplary graph 800 of image data 802 produced when the current scan frequency returns the highest pixel value 308. Thus, no PLL 108 frequency adjustment is needed.

FIG. 9 is a graphical illustration of an exemplary graph 900 of image data 902 produced when the lower scan frequency returns the highest pixel value 308. Thus, the resonant frequency of the sensor 102 is lower than the current frequency. The PLL 108 frequency is then lowered by the compensation process.

FIG. 10 is a graphical illustration of an exemplary graph 1000 of image data 1002 produced when the higher scan frequency returns the highest pixel value 308. Thus, the resonant frequency of the sensor 102 is higher than the current frequency. The PLL 108 frequency is then raised by the compensation process.

Exemplary Methods

Figure 11:
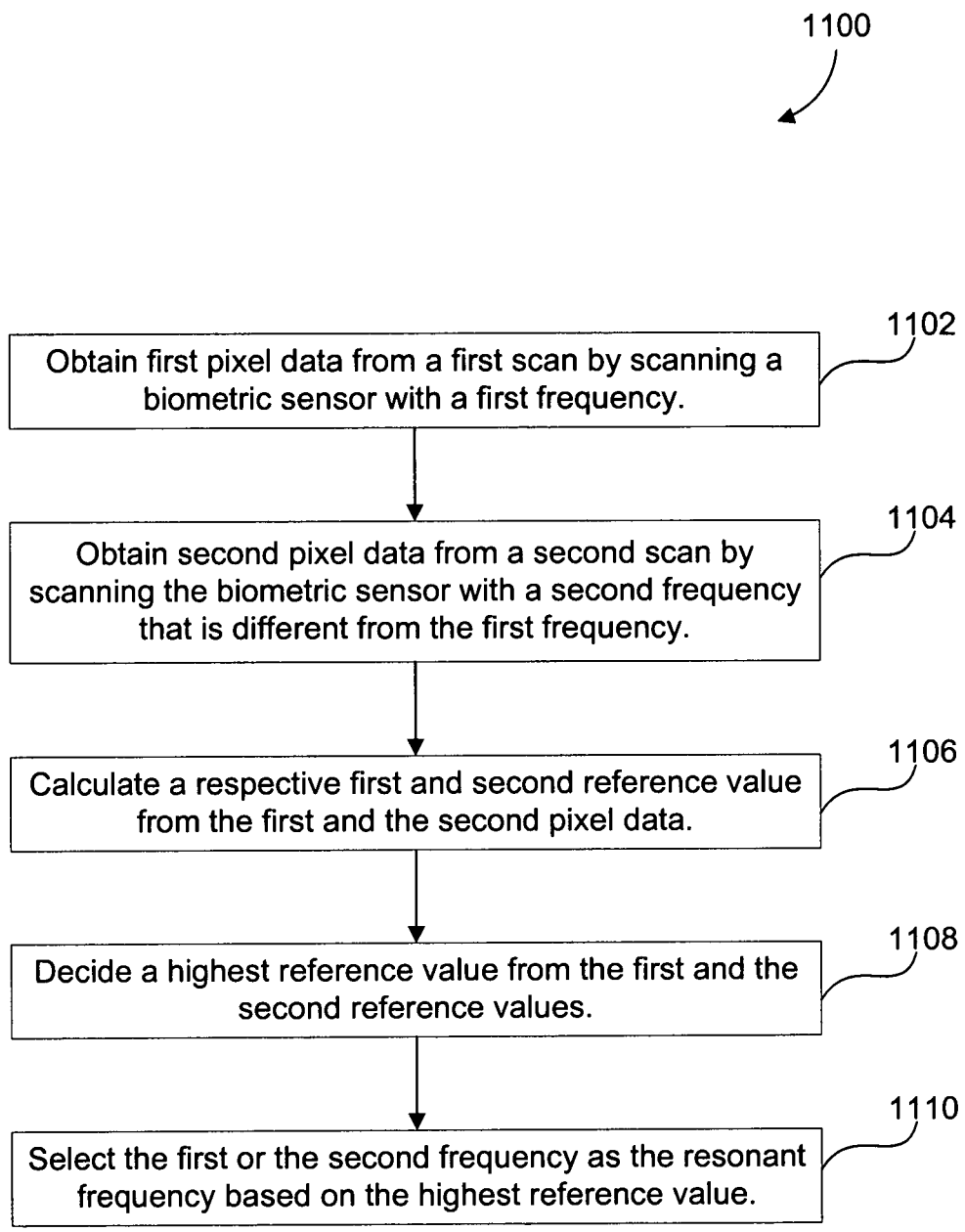
FIG. 11 is an exemplary flowchart of a method for determining a resonant frequency of a biometric sensor.

FIG. 11 is a flowchart of an exemplary method 1100 for determining the resonant frequency of the biometric sensor 102. In step 1102, first pixel data is obtained from a first scan by scanning a biometric sensor with a first frequency. In step 1104, second pixel data is obtained from a second scan by scanning the biometric sensor with a second frequency that is different from the first frequency.

In step 1106, a respective first and second reference value is calculated from the first and the second pixel data. Optionally, the first pixel data can have first pixel values. The calculating can add the first pixel values to calculate the first reference value. Further, the calculating can find a mean of the pixel values to calculate the first reference value. Similarly, the second pixel data can have second pixel values. The calculating can add the second pixel values to calculate the second reference value. Further, the calculating can find a mean of the second pixel values to calculate the second reference value.

In step 1108, a highest reference value from the first and the second reference values is determined. In step 1110, the first or the second frequency is selected as the resonant frequency based on the highest reference value. A phase locked loop (PLL) frequency can be set to substantially the resonant frequency. Further, the frequency of the PLL can be set to a harmonic or a sub-harmonic of the resonant frequency.

The method 1100 can further include steps to reduce scanning time. The first reference value is compared to a first threshold value and a second threshold value. The method stops obtaining first pixel data if, over time, the first reference value is initially greater than the first threshold and subsequently less than the second threshold.

The method 1100 can also further include steps to compensate for changes in resonant frequency. Third pixel data from a third scan is obtained by scanning the biometric sensor with a third frequency that is less than the resonant frequency. Fourth pixel data is obtained from a fourth scan by scanning the biometric sensor with a fourth frequency that is greater than the resonant frequency. Fifth pixel data is obtained from a fifth scan by scanning the biometric sensor with the resonant frequency. A respective third, fourth, and fifth reference values are calculated from the third, the fourth and the fifth pixel data. A revised highest reference value is decided from the third, the fourth, and the fifth reference values. The third, the fourth, or the fifth frequency is selected as a revised resonant frequency. A PLL frequency can be adjusted to substantially equal the revised resonant frequency.

The method 1100 can further include steps to revise the resonant frequency determination, in other words, to fine-tune the determination. Third pixel data is obtained from a third scan by scanning the biometric sensor with a third frequency. Fourth pixel data is obtained from a fourth scan by scanning the biometric sensor with a fourth frequency that is different from the third frequency. The first and the second frequencies are in a first plurality of frequencies having a first frequency spacing. The third and the fourth frequencies are in a second plurality of frequencies having a second frequency spacing less than the first frequency spacing. Respective third and fourth reference values are calculated from the third and the fourth pixel data. A revised highest reference value from the third and the fourth reference values is decided. The third or the fourth frequency is selected as a revised resonant frequency based on the revised highest reference value.

The methods and/or processes herein (i.e., the system and/or process listed above or any part(s) or function(s) thereof) can be implemented using hardware, software or a combination thereof and can be implemented in one or more computer systems or other processing systems. However, the manipulations performed by the present invention were often referred to in terms, such as adding or comparing, which are commonly associated with mental operations performed by a human operator. No such capability of a human operator is necessary, or desirable in most cases, in any of the operations described herein which form part of the present invention. Rather, the operations are machine operations. Useful machines for performing the operation of the present invention include general purpose digital computers and/or similar devices.

Figure 12:
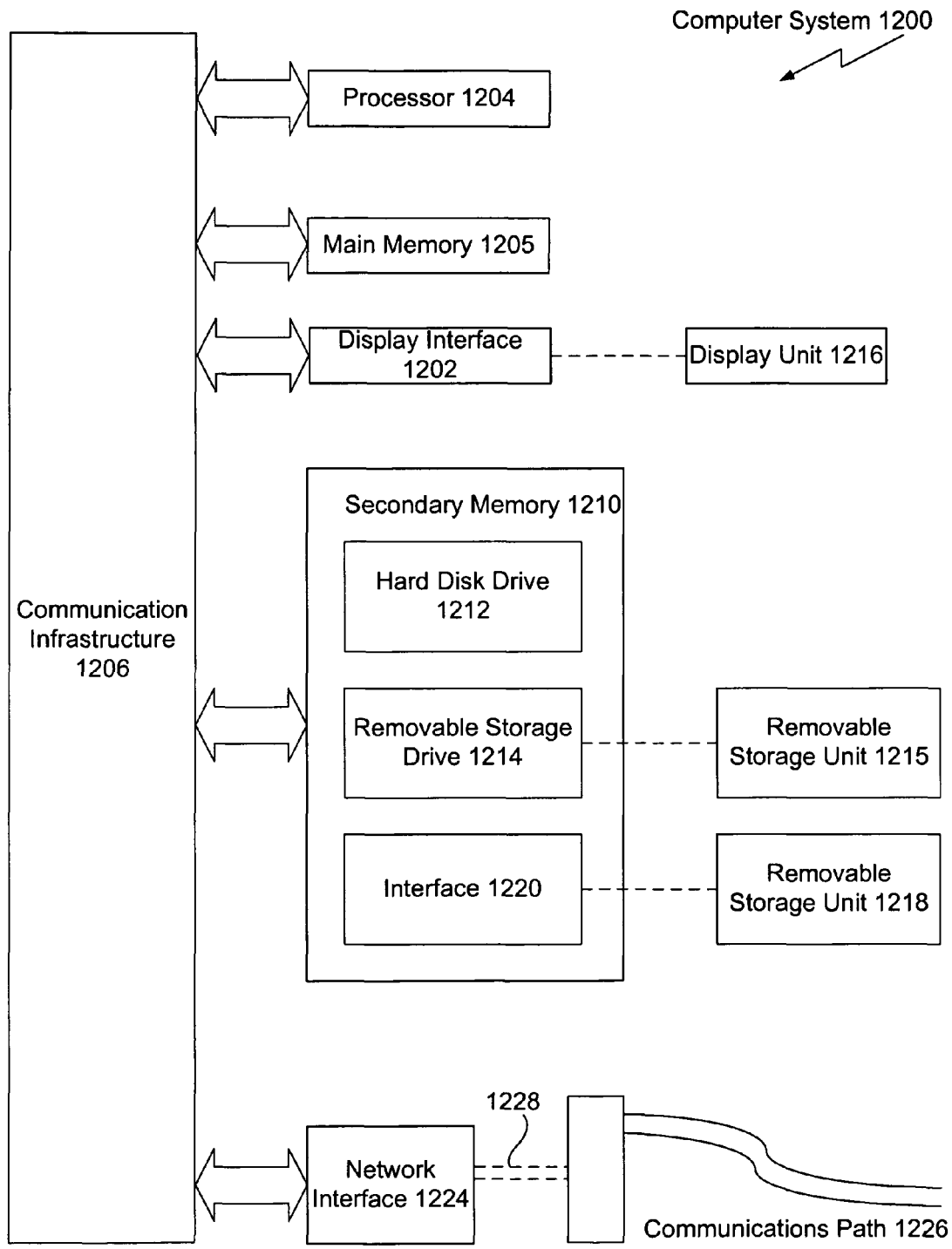
FIG. 12 is a block diagram illustration of an exemplary computer system upon which the present invention can be implemented.

In one embodiment, the invention is directed toward one or more computer systems capable of carrying out the functionality described herein. An example of a computer system 1200 is shown in FIG. 12.

The computer system 1200 includes a processor 1204, such as the processor 104. The processor 1204 is connected to a communication infrastructure 1206 (e.g., a communications bus, cross-over bar, or network). Various software embodiments are described in terms of this exemplary computer system. After reading this description, it will become apparent to a person skilled in the relevant art(s) how to implement the invention using other computer systems and/or architectures.

The computer system 1200 can include a display interface 1202 that forwards graphics, text, and other data from the communication infrastructure 1206 (or from a frame buffer not shown) for display on a display unit 1216.

The computer system 1200 also includes a main memory 1208, preferably random access memory (RAM), and can also include a secondary memory 1210. The secondary memory 1210 can include, for example, a hard disk drive 1212 and/or a removable storage drive 1214, representing a floppy disk drive, a magnetic tape drive, an optical disk drive, an information storage device, etc. The removable storage drive 1214 reads from and/or writes to a removable storage unit 1218. The removable storage unit 1218 represents a floppy disk, a magnetic tape, an optical disk, etc. which is read by, and written to, by the removable storage drive 1214. The removable storage unit 1218 includes a computer readable storage medium having stored therein computer software and/or data.

In alternative embodiments, the secondary memory 1210 can include other similar devices for allowing computer programs or other instructions to be loaded into the computer system 1200. Such devices can include, for example, the removable storage unit 1218 and an interface 1220. Examples of the secondary memory 1210 include a program cartridge and cartridge interface, a removable memory chip (such as an erasable programmable read only memory (EPROM), and/or programmable read only memory (PROM)) with an associated socket, and the removable storage unit 1218 and/or the interface 1220, which allow software and data to be transferred from the removable storage unit 1218 to the computer system 1200.

The computer system 1200 can also include a communications interface 1224. The communications interface 1224 allows software and data to be transferred between the computer system 1200 and an external device 1230. Examples of the communications interface 1224 can include a modem, a network interface (such as an Ethernet card), a communications port, a Personal Computer Memory Card International Association (PCMCIA) slot and card, etc. Software, data, and processor instructions transferred via the communications interface 1224 can be in a form of signals which can be electronic, electromagnetic, optical or other signals capable of being received by the communications interface 1224. The signals are provided to the communications interface 1224 via a communications path (e.g., channel) 1226. The communications path 1226 carries signals and can be implemented using wire or cable, fiber optics, a telephone line, a cellular link, a radio frequency (RF) link, and/or other communications channels.

In this document, the terms "computer program medium," "computer readable medium," and "computer usable medium" are used to generally refer to media such as the removable storage drive 1214, a hard disk installed in the hard disk drive 1212, and signals. These computer program products provide software to the computer system 1200. The invention is directed to such computer program products.

Computer programs (also referred to as computer control logic) are stored in the main memory 1208 and/or the secondary memory 1210. The computer programs can also be received via the communications interface 1224. Such computer programs, when executed, enable the computer system 1200 to perform the features of the present invention, as discussed herein. In particular, the computer programs, when executed, enable the processor 1204 to perform the features of the present invention. Accordingly, such computer programs represent controllers of the computer system 1200.

In an embodiment where the invention is implemented using software, the software can be stored in a computer program product and loaded into the computer system 1200 using the removable storage drive 1214, the hard drive 1212 or the communications interface 1224. The control logic (software), when executed by the processor 1204, causes the processor 1204 to perform the functions of the invention as described herein.

In another embodiment, the invention is implemented primarily in hardware using, for example, hardware components such as application specific integrated circuits (ASICs). Implementation of the hardware state machine so as to perform the functions described herein will be apparent to persons skilled in the relevant art(s). In yet another embodiment, the invention is implemented using a combination of both hardware and software.

CONCLUSION

Examples that incorporate the features of this invention are described herein. These examples are described for illustrative purposes only, and are not limiting. Other embodiments are possible. Such other embodiments will be apparent to persons skilled in the relevant art(s) based on the teachings contained herein. Thus, the breadth and scope of the present invention is not limited by any of the above-described exemplary embodiments, but must be defined only in accordance with the following claims and their equivalents.

The description fully reveals the nature of the invention that others can, by applying knowledge within the skill of the art, readily modify and/or adapt for various applications the exemplary embodiments, without undue experimentation, and without departing from the general concept of the present invention. Therefore, such adaptations and modifications are intended to be within the meaning and range of equivalents of the disclosed embodiments, based on the teaching and guidance presented herein. It is to be understood that phraseology and terminology herein is for the purpose of description and not for limitation, such that the terminology and phraseology of the present specification is to be interpreted by the skilled artisan in light of the teachings and guidance herein.

What we claim is:

1. A method for determining a resonant frequency of a non-optical biometric sensor, comprising:
    obtaining first pixel data from a first scan by scanning the non-optical biometric sensor with a first frequency;
    obtaining second pixel data from a second scan by scanning the biometric sensor with a second frequency that is different from the first frequency;
    calculating a respective first and second reference value from the first and the second pixel data;
    deciding a highest reference value from the first and the second reference values; and
    selecting the first or the second frequency as the resonant frequency based on the highest reference value.

2. The method of claim 1, wherein the first pixel data comprises pixel values and the calculating step further comprises adding the pixel values to calculate the first reference value.

3. The method of claim 1, wherein the first pixel data comprises pixel values and the calculating step further comprises finding a mean of the pixel values to calculate the first reference value.

4. The method of claim 1, further comprising setting a phase locked loop frequency to the resonant frequency.

5. The method of claim 1, further comprising:
    comparing the first reference value to a first threshold value and a second threshold value; and
    stopping the obtaining first pixel data step if the first reference value is greater than the first threshold and less than the second threshold.

6. The method of claim 1, further comprising:
    obtaining third pixel data from a third scan by scanning the biometric sensor with a third frequency that is less than the resonant frequency;
    obtaining fourth pixel data from a fourth scan by scanning the biometric sensor with a fourth frequency that is greater than the resonant frequency;
    obtaining fifth pixel data from a fifth scan by scanning the biometric sensor with the resonant frequency;
    calculating a respective third, fourth, and fifth reference values from the third, the fourth and the fifth pixel data;
    deciding a revised highest reference value from the third, the fourth, and the fifth reference values; and
    selecting the third, the fourth, or the fifth frequency as a revised resonant frequency.

7. The method of claim 6, further comprising:
    adjusting a phase locked loop frequency to the revised resonant frequency.

8. The method of claim 1, further comprising:
    obtaining third pixel data from a third scan by scanning the biometric sensor with a third frequency;
    obtaining fourth pixel data from a fourth scan by scanning the biometric sensor with a fourth frequency that is different from the third frequency;
    wherein the first and the second frequencies are in a first plurality of frequencies having a first frequency spacing;
    wherein the third and the fourth frequencies are in a second plurality of frequencies having a second frequency spacing less than the first frequency spacing;
    calculating respective third and fourth reference values from the third and the fourth pixel data;
    deciding a revised highest reference value from the third and the fourth reference values; and
    selecting the third or the fourth frequency as a revised resonant frequency based on the revised highest reference value.

9. A non-transitory computer-readable medium containing instructions for controlling at least one processor to determine a resonant frequency of a non-optical biometric sensor by a method, comprising:
    obtaining first pixel data from a first scan by scanning the non-optical biometric sensor with a first frequency;
    obtaining second pixel data from a second scan by scanning the biometric sensor with a second frequency that is different from the first frequency;
    calculating a respective first and second reference value from the first and the second pixel data;
    deciding a highest reference value from the first and the second reference values; and
    selecting the first or the second frequency as the resonant frequency based on the highest reference value.

10. The non-transitory computer-readable medium of claim 9, wherein the method further comprises:
    wherein the first pixel data comprises pixel values and the calculating step further comprises adding the pixel values to calculate the first reference value.

11. The non-transitory computer-readable medium of claim 9, wherein the method further comprises:
    wherein the first pixel data comprises pixel values and the calculating step further comprises finding a mean of the pixel values to calculate the first reference value.

12. The non-transitory computer-readable medium of claim 9, wherein the method further comprises:
setting a phase locked loop frequency to the resonant frequency.

13. The non-transitory computer-readable medium of claim 9, wherein the method further comprises:
comparing the first reference value to a first threshold value and a second threshold value; and
stopping the obtaining first pixel data step if the first reference value is greater than the first threshold and less than the second threshold.

14. The non-transitory computer-readable medium of claim 9, wherein the method further comprises:
obtaining third pixel data from a third scan by scanning the biometric sensor with a third frequency that is less than the resonant frequency;
obtaining fourth pixel data from a fourth scan by scanning the biometric sensor with a fourth frequency that is greater than the resonant frequency;
obtaining fifth pixel data from a fifth scan by scanning the biometric sensor with the resonant frequency;
calculating a respective third, fourth, and fifth reference values from the third, the fourth and the fifth pixel data;
deciding a revised highest reference value from the third, the fourth, and the fifth reference values; and
selecting the third, the fourth, or the fifth frequency as a revised resonant frequency.

15. The non-transitory computer-readable medium of claim 9, wherein the method further comprises:
adjusting a phase locked loop frequency to the revised resonant frequency.

16. The non-transitory computer-readable medium of claim 9, wherein the method further comprises:
obtaining third pixel data from a third scan by scanning the biometric sensor with a third frequency;
obtaining fourth pixel data from a fourth scan by scanning the biometric sensor with a fourth frequency that is different from the third frequency;
wherein the first and the second frequencies are in a first plurality of frequencies having a first frequency spacing;
wherein the third and the fourth frequencies are in a second plurality of frequencies having a second frequency spacing less than the first frequency spacing;
calculating respective third and fourth reference values from the third and the fourth pixel data;
deciding a revised highest reference value from the third and the fourth reference values; and
selecting the third or the fourth frequency as a revised resonant frequency based on the revised highest reference value.

17. A biometric sensing apparatus, comprising:
a piezoelectric sensing device; and
a processor coupled to the piezoelectric device;
wherein the processor is configured to:
obtain first pixel data from a first scan by scanning the biometric sensor with a first frequency;
obtain second pixel data from a second scan by scanning the biometric sensor with a second frequency that is different from the first frequency;
calculate a respective first and second reference value from the first and the second pixel data;
decide a highest reference value from the first and the second reference values; and
select the first or the second frequency as the resonant frequency based on the highest reference value.

18. The method of claim 1 wherein said resonant frequency is in the MHz range.

19. The non-transitory computer of claim 9 wherein said resonant frequency is in the MHz range.

20. A system for selecting a frequency for resonating a piezoelectric sensing device comprising:
a piezoelectric sensing device which in response to an applied selected frequency provides pixels having pixel values representing an image of a fingerprint of a finger when placed upon said sensing device; and
a frequency generating device for applying to said piezoelectric sensing device different frequencies to provide different ones of said image in which one of said different frequencies is said selected frequency when the image associated with said one of said different images has more pixels of higher values than said different ones of said image associated with any other of said different frequencies.

21. The system according to claim 20 further comprising a processor for controlling said frequency generating device to apply to said piezoelectric sensing device different frequencies and process each of said different ones of said image to determine when the image associated with said one of said different images has more pixels of higher values than said different ones of said image associated with any other of said different frequencies.

22. The system according to claim 19 further comprising a processor for controlling said frequency generating device to apply to said piezoelectric sensing device each of said different frequencies spaced from each other in succession until a next frequency after said selected frequency is applied.

23. The system according to claim 19 further comprising a processor for controlling said frequency generating device to apply to said piezoelectric sensing device each of said different frequencies spaced from each other in succession.

24. The system according to claim 23 wherein said selected frequency is said one of said different frequencies applied when the image associated with said one of said different frequencies has more pixels of higher values than the image associated with the next successive one of said different frequencies when the pixel values of the image associated with said one of said different frequencies is represented by a first reference value and said first reference value is higher than both a first threshold value and a second threshold value, said second threshold value is lower than said first threshold value, and when the pixels values of the image associate with the next successive one of said different frequencies applied after said selected frequency is represented by a second reference value, and said second reference value is below said second threshold value.

25. The system according to claim 21 wherein said frequency generating device is part of said processor.

26. A system for selecting a frequency for resonating a piezoelectric sensing device comprising:
a piezoelectric sensing device which in response to an applied resonant frequency provides pixels having pixel values representing an image of a fingerprint of a finger when placed upon said sensing device; and
a frequency generating device for first applying to said piezoelectric sensing device different frequencies spaced from each other in succession over a first range of frequencies to provide different ones of said image in which one of said different frequencies over said first range is a selected frequency when the image associated with said one of said different images has more pixels of higher values than said different ones of said image associated with any other of said different frequencies over said first range, and then applying to said piezoelectric sensing device different frequencies spaced from each other in succession over a second range of frequencies to provide different ones of said image in which one of said different frequencies in said second range is said resonant frequency when the image associated with said one of said different images has more pixels of higher values than said different ones of said image associated with any other of said different frequencies in said second range, and said second range of frequencies lies within said first range of frequencies and spaced closer to each other than said different frequencies in said first range.

27. The system according to claim 26 further comprising a processor for controlling said frequency generating device to apply to said piezoelectric sensing device each of said different frequencies spaced from each other in succession in said first range until a next frequency after said selected frequency is applied, and to apply to said piezoelectric sensing device each of said different frequencies spaced from each other in succession in said second range until a next frequency after said resonant frequency is applied.

* * * * *